(12) United States Patent
Hugg (10) Patent No.: US 11,723,608 B2
(45) Date of Patent: Aug. 15, 2023

(54) TRANSFORMABLE GAMMA CAMERAS

(71) Applicant: KROMEK GROUP, PLC

(72) Inventor: James W. Hugg, Mars, PA (US)

(73) Assignee: KROMEK GROUP. PLC, Sedgefield (GB)

( * ) Notice: Subject to any disclaimer, the term of this patent is extended or adjusted under 35 U.S.C. 154(b) by 295 days.

(21) Appl. No.: 16/944,952

(22) Filed: Jul. 31, 2020

(65) Prior Publication Data
US 2020/0352527 A1 Nov. 12, 2020

Related U.S. Application Data

(63) Continuation of application No. 16/324,038, filed as application No. PCT/US2017/045968 on Aug. 8, 2017, now abandoned.

(60) Provisional application No. 62/372,007, filed on Aug. 8, 2016.

(51) Int. Cl.
*A61B 6/03* (2006.01)
*G01T 1/166* (2006.01)
(Continued)

(52) U.S. Cl.
CPC ............ *A61B 6/037* (2013.01); *A61B 6/0414* (2013.01); *A61B 6/06* (2013.01); *A61B 6/4233* (2013.01);
(Continued)

(58) Field of Classification Search
CPC ....... G01T 1/1642; G01T 1/166; A61B 6/037; A61B 6/4258; A61B 6/4458
See application file for complete search history.

(56) References Cited

U.S. PATENT DOCUMENTS 5,293,044 A   3/1994   Klingenbeck-Regn et al.
5,929,446 A   7/1999   Plummer et al.
(Continued)

FOREIGN PATENT DOCUMENTS

CN   105395208 A   3/2016

OTHER PUBLICATIONS

ISA/US, Commissioner for Patents, International Search Report, dated Oct. 18, 2017, 2 pages, The United States Patent and Trademark Office.
(Continued)

*Primary Examiner* — Boniface Ngathi N
*Assistant Examiner* — Milton Truong
(74) *Attorney, Agent, or Firm* — Ference & Associates LLC (57) ABSTRACT

One embodiment provides a gamma camera system, including: a stand, a rotatable gantry supported by the stand, and a transformable gamma camera connected by mechanical supports to the rotatable gantry and comprising groups of tiled arrays of gamma detectors and a collimator for each group of tiled arrays of gamma detectors; the transformable gamma camera being configured to subdivide into a plurality of subdivided gamma cameras, each of the subdivided gamma cameras having at least one of the groups of tiled arrays of gamma detectors and corresponding collimator, wherein the subdivision into a plurality of subdivided gamma cameras facilitates contouring with a region of interest for a spatial resolution. Other embodiments are described and claimed.

19 Claims, 8 Drawing Sheets

(51) Int. Cl.
*A61B 6/04* (2006.01)
*A61B 6/00* (2006.01)
*G01T 1/164* (2006.01)
*G01T 1/202* (2006.01)
*A61B 6/06* (2006.01)
*G01T 1/20* (2006.01)

(52) U.S. Cl.
CPC .......... *A61B 6/4258* (2013.01); *A61B 6/4291* (2013.01); *A61B 6/4411* (2013.01); *A61B 6/4458* (2013.01); *A61B 6/501* (2013.01); *A61B 6/502* (2013.01); *A61B 6/503* (2013.01); *G01T 1/166* (2013.01); *G01T 1/1642* (2013.01); *G01T 1/202* (2013.01); *G01T 1/2006* (2013.01); *G01T 1/2023* (2013.01)

(56) References Cited

U.S. PATENT DOCUMENTS

| | | | |
|---|---|---|---|
| 6,055,450 A * | 4/2000 | Ashburn | A61B 6/4258 250/363.04 |
| 6,455,856 B1 | 9/2002 | Gagnon | |
| 7,291,841 B2 | 11/2007 | Nelson et al. | |
| 2006/0049362 A1 | 3/2006 | Friedman et al. | |
| 2010/0038548 A1 | 2/2010 | Guerin et al. | |
| 2010/0260316 A1 | 10/2010 | Stein et al. | |
| 2010/0329418 A1* | 12/2010 | Blevis | A61B 6/037 378/37 |
| 2011/0270078 A1* | 11/2011 | Wagenaar | G01R 33/481 600/411 |
| 2013/0320222 A1* | 12/2013 | Abenaim | A61B 6/032 250/366 |
| 2013/0320234 A1 | 12/2013 | Volokh et al. | |
| 2015/0094573 A1 | 4/2015 | Bouhnik et al. | |
| 2015/0119704 A1 | 4/2015 | Roth et al. | |
| 2015/0177392 A1 | 6/2015 | Hefetz et al. | |
| 2015/0276949 A1 | 10/2015 | Grobshtein et al. | |

OTHER PUBLICATIONS

European Patent Office, Extended Search Report, Feb. 21, 2020, 8 pages, European Patent Office, Munich Germany.
European Patent Office, Examination Report, dated Dec. 7, 2022, 6 pages, European Patent Office, Munich Germany.

* cited by examiner

TRANSFORMABLE GAMMA CAMERAS

CROSS-REFERENCE TO RELATED APPLICATION

This application is a continuation application of U.S. patent application Ser. No. 16/324,038 filed on Feb. 7, 2019 and titled "Transformable Gamma Cameras," which is a national phase application of PCT/US17/45968 filed on Aug. 8, 2017 and titled "Transformable Gamma Cameras," and claims priority from and benefit of U.S. Provisional Patent Application No. 62/372,007 filed on Aug. 8, 2016 and titled "Transformable Gamma Cameras," all of which the subject matter of which is hereby incorporated by reference in its entirety.

FIELD OF THE INVENTION

The principle application addressed by this disclosure is Gamma Cameras, in general, and specifically Nuclear Medicine (aka "molecular Imaging") which employs Single-Photon Emission Computed Tomography (SPECT) following injection of a radioisotope-labelled tracer (molecular imaging agent). The emitted gamma photons are imaged by a gamma camera, or preferably, a plurality of gamma cameras. In the case of single-photon emission (as in SPECT), a collimator (parallel hole, focusing, or multiple pinhole) is integral to the gamma camera. It is also possible to use a Compton scattering detector (also known as "electronic collimation"), such as a plurality of Si position sensitive detectors, with each gamma camera to detect Compton scattered events and to form images by 3D reconstruction. In other applications of gamma cameras, such as monitoring particle beam radiation therapy, security detection of radioactive sources, or astronomical mapping of gamma photon sources, coded aperture collimation and planar gamma photon imaging may be employed. The examples are only illustrative; this invention applies to all applications of gamma cameras.

This invention provides practical designs for pixelated-detector based gamma cameras and pixelated-detector-based gamma camera systems. In particular, this invention can be applied beneficially to gamma cameras built from pixelated semiconductor direct conversion CZT (CdZnTe) gamma detectors.

BACKGROUND OF THE INVENTION

Gamma cameras, previously also known as scintillation cameras or Anger cameras, have been used to image gamma photon emission in a technique known generally as scintigraphy. They are applied in nuclear medicine imaging to view images of a body containing medically injected, inhaled, or ingested radiopharmaceuticals emitting gamma photons. They can also be used in security or astronomy applications to detect and image gamma photons arising from radioactive sources or astrophysical sources. Hal Anger developed the first gamma camera in 1957 and variations on his design are still widely used today.

A typical scintillation gamma camera consists of a large flat rectangular crystal (typically about 54 cm×40 cm×1 cm) of sodium iodide with thallium doping, labelled NaI(Tl), in a sealed container that prevents moisture and visible light from reaching the crystal. One face has a transparent glass window or light guide. The crystal scintillates when a gamma photon strikes it and the scintillation light can escape through the glass window, where an array of optically-coupled photodetectors, such as vacuum photomultiplier tubes (PMTs) or silicon photomultipliers, are typically coupled through optical gel. The location of a gamma photon interaction in the NaI crystal are determined by a center-of-gravity type weighting of the voltage responses of multiple PMTs that detect the scintillation light.

A gamma camera is typically coupled with a collimator (for example: parallel hole, focused, multiple pinhole, or coded aperture) that acts as a lens for forming a planar projection image. In SPECT, used in nuclear medicine, a 3D image is formed by moving the gamma camera to multiple different angular positions around the patient, acquiring planar projections at each position, and then reconstructing a 3D image of the gamma emission source distribution using various techniques, such as filtered back-projection or iterative maximum likelihood estimation reconstruction. Commercial SPECT systems most commonly consist of two scintillator (usually NaI) gamma cameras mounted on a gantry with a patient table positioned between the slowly rotating gamma cameras.

This invention addresses several limitations of current commercial solutions and prior patents. In particular, the basic technology used in gamma cameras has not changed substantially since 1957, except that computers have increased the efficiency of the data acquisition and image reconstruction. One significant problem with state-of-the-art systems is that they are usually designed as "general purpose" SPECT systems in which many compromises have been made to accommodate different clinical applications, such as bone, brain, heart, or breast imaging. There are dedicated cardiac SPECT systems on the market, and dedicated planar breast gamma imaging systems, and there have been brain SPECT systems devised.

This invention concerns the introduction of pixelated gamma detectors arrayed as a gamma camera. By way of illustration, pixelated semiconductor Cadmium-Zinc-Telluride (CZT) detectors will be referenced, although similar considerations apply to other semiconductor gamma detectors, such as Cadmium-Telluride (CdTe) and Mercuric Iodide (HgI), or to pixelated scintillator detectors. These pixelated semiconductor detectors have many performance advantages over the monolithic scintillator and PMT prior art, but they also have the disadvantage of having a higher cost than the almost 60-year old prior art. This invention addresses ways to increase the clinical utility and efficiency of pixelated semiconductor gamma cameras by enabling them to adapt and transform to more optimal geometries for various clinical applications.

Figure 1:
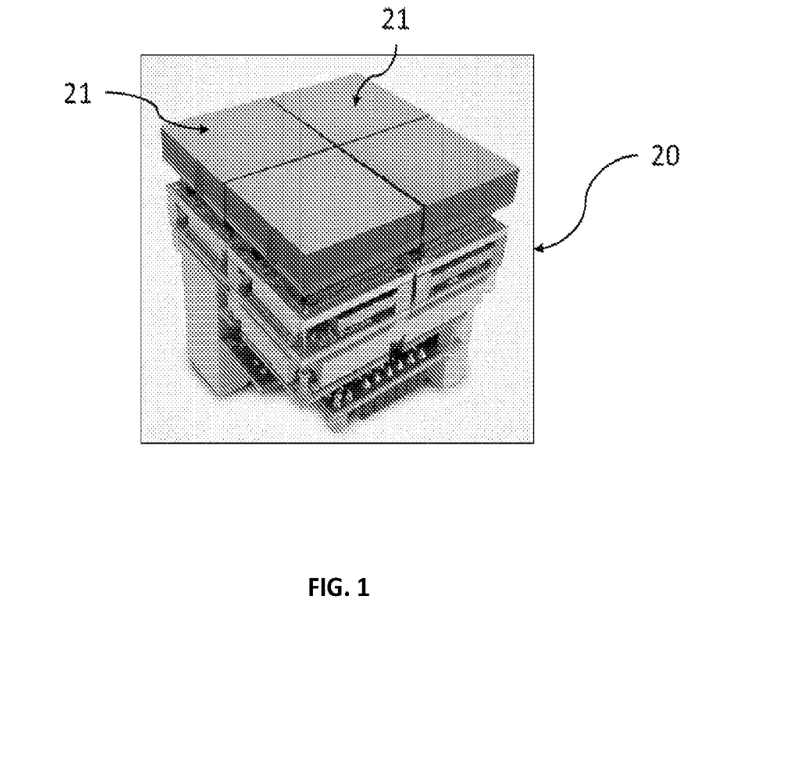
FIG. 1 is a pixelated CZT detector module of the preferred embodiment of the invention.

By way of example, we will discuss a preferred embodiment of a transformable CZT gamma camera consisting of an array of modular pixelated CZT detectors (called D-Matrix™) that we have designed and tested. The basic module is shown in FIG. 1 and consists of four CZT gamma modules (GM) 21 in a 2×2 array comprising one aggregator module (AM) 20. Each II 20 is 4.4 cm square and provides digital signal output including 2D location (module and pixel numbers or, preferably, x and y) and energy for each gamma photon detection event. Optionally, a 3D location including depth of interaction in the CZT crystal can also be provided by reading the cathode signal as well as the pixelated anode signals. One skilled in the art will appreciate that the AM 20 includes ASICs (application-specific integrated circuits), ADCs (analog to digital converters), and FPGAs (field-programmable gate arrays) as well as supporting electronics. Table 1 following contains the essential characteristics of each CZT gamma detector aggregator module 20.

TABLE 1

Features of a DMatrix ™ CZT gamma detector aggregator module (AM) 20, as shown in FIG. 1.

| Feature | Performance |
| --- | --- |
| Aggregator Module detection area | 4.4 cm × 4 4 cm |
| Pixel pitch | 2 mm |
| CZT thickness | 0.5 cm (or optional 1.0 cm) |
| Footprint | Tileable on 4 sides |
| Energy range | 30 keV to 400 keV |
| Operating temperature range | 18° C. to 25° C. ambient |
| Data output (list mode) | x, y, energy, (optional: z [depth of interaction] and various event timings) |
| API | Software for acquisition computer interface |

Figure 2:
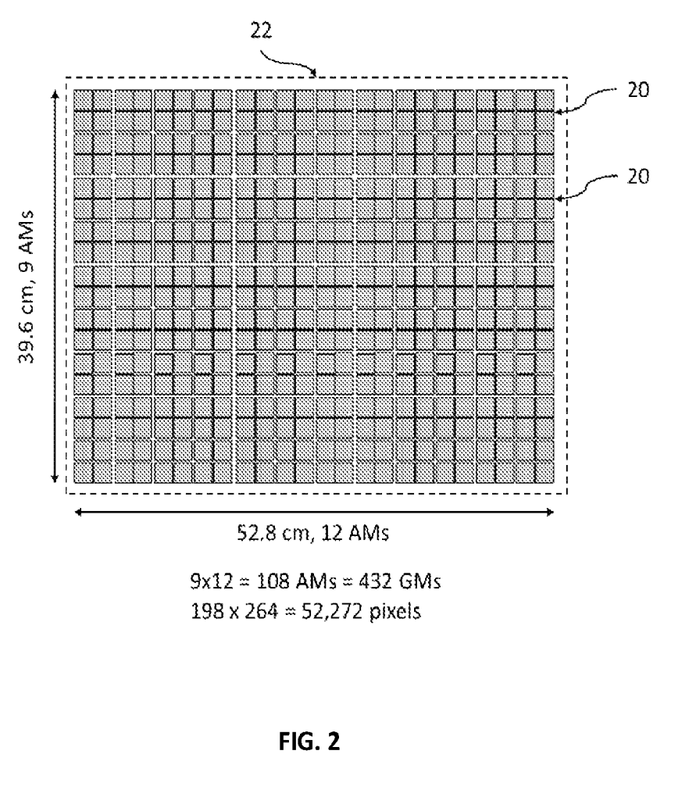
FIG. 2 is an illustration of an array of the CZT detector modules of FIG. 1 in a size appropriate for a general purpose flat panel SPECT gamma camera.

By way of further example, we will discuss a gamma camera 22 composed of D-Matrix™ aggregator modules 20 arrayed in a size compatible with a general-purpose SPECT system as depicted in FIG. 2. In the illustration, nine AMs 20 are arrayed in each of 12 columns, each 39.6 cm long and 4.4 cm wide. The 12 adjacent columns comprise a camera 52.8 cm wide. Thus, there are a total of nine×12=108 AM 20, and 4×108=432 GM 21. Since each GM 21 has 121 pixels, the general-purpose gamma camera 22 in FIG. 2 has 52,272 pixels, each two mm square. Some of the advantages of a CZT gamma camera compared to a scintillator gamma camera can be seen in Table 2 following.

TABLE 2

Comparison of typical scintillator gamma camera to a CZT gamma camera composed of an array of D-Matrix ™ CZT detector aggregator modules DEI) 20.

| Compared Metric | Typical NaI & PMTs cameras | modular CZT cameras |
| --- | --- | --- |
| Detector Crystal Thickness | 0.95 cm thick NaI | 0.5 cm thick CZT or 1.0 cm thick CZT (option) |
| Camera Useful Field of View | 40.6 cm × 54 cm | 39.6 cm × 52.8 cm (no dead edges) |
| Intrinsic Spatial Resolution | 3.3 mm FWHM Gaussian | 2.0 mm square pixels |
| Intrinsic Pixels per Camera (Space-Bandwidth Product) | 20,132 with Gaussian overlap | 52,272 square, no overlap |
| Intrinsic Energy Resolution | <9.6% FWHM @ 140 keV | <4.5% FWHM @ 140 keV |

Table 2 shows that CZT detectors can be arrayed in a camera size similar to a typical commercial gamma camera (most are about 40 cm axial×54 cm transaxial). The 5 mm thickness of CZT is chosen to provide a similar stopping power to a typical 0.95 cm (⅜") thick NaI scintillator. This thickness is adequate for the most common medical isotopes, such as Tc-99m (140 keV), Tl-201 (70 keV), Xe-133 (81 keV), Ga-67 (90 keV), and I-123 (159 keV). Increasing the CZT thickness to 1.0 cm will increase the stopping power and thus the detection efficiency for higher energy medical isotopes, such as In-111 (171 & 245 keV) and I-131 (364 keV), although they can be detected with 5 mm thick CZT, albeit less efficiently.

The intrinsic spatial resolution of a CZT gamma camera 22 is about 1.7 times better than a typical scintillator gamma camera resulting in 2.7 times more pixels in the same detector area. Moreover, the pixelated CZT gamma camera has no dead edges compared to the scintillation camera which has unusable ("dead") edges about half the diameter of the PMTs wherein the Anger position determination is ineffective. Thus, the edges must be masked off and not used for imaging. Furthermore, a scintillation gamma camera has a nonuniform performance wherein the central field of view CFOV performs significantly better than the peripheral ("useful") field of view UFOV. In a CZT gamma camera the performance is uniform across the full surface, so the CFOV and UFOV performance is equal. Furthermore, the CZT pixels are square and non-overlapping (except for a small amount of charge sharing), while the scintillator pixels are Gaussian with considerable overlap with neighboring pixels. Finally, the energy resolution is typically 2.4 or more times better, resulting in a better discrimination against scattered gamma photons which blur SPECT images.

Another advantage offered by tiled array semiconductor gamma cameras is that they can be advantageously deployed as sparsely populated arrays of detectors, as described in U.S. patent application Ser. No. 15/473,336 filed on Mar. 29, 2017 and titled "Sparse Acquisition Gamma Cameras," the subject matter of which is hereby incorporated by reference in its entirety. In regard to the transformable gamma cameras of the present specification, it should be understood that the tiled array of gamma detectors may comprise a sparsely populated tiled array of gamma detectors, as well as the case wherein the tiled array of gamma detectors is fully populated.

BRIEF SUMMARY OF THE INVENTION

One fundamental problem addressed by the present invention is that the gamma cameras for a general-purpose SPECT system are designed for a subset of clinical applications that require large planar projections of the body. This requires that the field-of-view (FOV) be about 40 cm (axial)×54 cm (transaxial) to enable planar whole-body bone imaging (with patient bed movement to multiple locations), lung ventilation imaging, and cardiac first-pass bolus imaging, for example. All other clinical applications of SPECT would be better served by a different configuration of smaller FOV gamma cameras.

One fundamental characteristic of this invention requires a modular design for pixelated CZT gamma cameras and takes advantage of the fact that there is no dead edge to the CZT detectors. The invention in one aspect is simply that the large FOV camera configuration can be transformed by subdividing the large modular camera into multiple smaller FOV gamma camera modules, independently positioned, and more suited geometrically for optimal SPECT imaging applications. By way of illustration, one embodiment of the present invention is to subdivide the large FOV camera into two equal half-FOV cameras, each about 40 cm (axial)×27 cm (transaxial). These half-FOV cameras can be positioned around the body in a more optimal configuration for various clinical SPECT imaging applications, as will be discussed.

The most significant performance advantage for the smaller FOV gamma cameras is that the imaging efficiency can be increased, leading to either shorter imaging times, or lower injected radiation doses, or a combination of both lower time and dose. Although this advantage will be apparent to those skilled in the art, an illustration will illuminate this conclusion. Consider heart imaging with standard 40 cm×54 cm gamma cameras. At any time during the acquisition, two planar projection images of the heart are being acquired, one on each of the two gamma cameras deployed in a standard SPECT system. In an embodiment of the present invention, these two full-FOV cameras will subdivide into four half-FOV cameras. At any time during the SPECT acquisition, there will now be four planar projection images of the heart being acquired simultaneously. This will essentially double the efficiency of the imaging, enabling use of lower time and/or dose without any other changes required.

In one embodiment, general purpose SPECT imaging can be optimized by subdividing two large-FOV gamma cameras into four half-FOV cameras and orbiting these four cameras around the body in a step-and-shoot or continuous acquisition sequence, while each camera individually can approach the body outline as closely as possible ("body contouring") to enhance spatial resolution.

In another embodiment, brain SPECT can be optimized by subdividing two large-FOV gamma cameras into four half-FOV cameras and orbiting these four cameras around the head in a step-and-shoot or continuous acquisition sequence, while each camera individually can approach the head outline as closely as possible to enhance spatial resolution.

In another embodiment, heart SPECT can be optimized by subdividing two large-FOV gamma cameras into four half-FOV cameras and orbiting these four cameras around the body in a step-and-shoot or continuous acquisition sequence, while each camera individually can approach the body outline as closely as possible to enhance spatial resolution and at the same time pointing toward the heart to increase efficiency.

In another embodiment, breast planar imaging (also known as molecular breast imaging) can be optimized by subdividing two large-FOV gamma cameras into four half-FOV cameras and placing a pair of half-FOV cameras in opposition next to each breast. Mild, non-painful compression between the two cameras will immobilize the breast. Multiple planar views can be acquired: for example, the two views most often used in mammography are the CC (cranial-caudal) and MLO (medial-lateral oblique) views. By imaging both breasts simultaneously, the clinical imaging time can be cut in half.

In a further embodiment of this present invention, the smaller-FOV gamma cameras can each wobble about their mechanical support axis to acquire projection data from a fan of angles. This acquisition strategy can reduce image reconstruction artifacts due to truncated views.

Another embodiment of the present invention is to separate the large FOV gamma camera into individual tiles (4.4 cm×4.4 cm for D-Matrix*^, by way of illustration), each with its own collimator and each positioned to optimize the efficiency and spatial resolution for the clinical application being addressed.

Another embodiment of this present invention is a method for employing a SPECT scanner with transformable gamma cameras designed and manufactured according to any of the mechanical embodiments described herein.

These embodiments are provided for illustration and those of ordinary skill in the art will understand that each large-FOV camera could favorably subdivide into three or more smaller-FOV cameras, each mechanically supported by the gantry and positioned around the patient. Furthermore, the use of three or more large-FOV transformable gamma cameras is possible, as are embodiments which combine standard non-transformable scintillator or semiconductor gamma cameras with transformable semiconductor gamma cameras.

BRIEF DESCRIPTION OF THE DRAWINGS

The organization and manner of the structure and operation of the invention, together with further objects and advantages thereof, may best be understood by reference to the following description, taken in connection with the accompanying non-scale drawings, wherein like reference numerals identify like elements in which.

DETAILED DESCRIPTION OF THE ILLUSTRATED EMBODIMENTS

While the invention may be subject to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

FIG. 1 shows a modular semiconductor direct conversion CZT gamma detector called D-Matrix™. This aggregator module (AM) 20 is composed of four CZT crystal detectors 21, each designated a gamma module (GM), each measuring about 2.2 cm×2.2 cm×0 5 cm thick. Each GM 21 may comprise a monolithic crystal or may comprise multiple tiles of CZT mounted in an abutting composite with small gaps between the tiles. The top GM 21 surface in FIG. 1 is the metallic cathode, which is typically monolithic but which can also be pixelated. Gamma photons generally enter the GUI from the cathode side of the CZT crystal. The lower surface of the GMs 21 has metallic anode pixels with a pitch of about two mm in an 11×11 pixel pattern for each CZT detector. The CZT is bonded to a substrate that provides mechanical stability and electrical connections to the read-out electronics boards, which include ASICs, one or more ADCs, and an FPGA. Negative DC bias voltage (about −500 V for 0.5 cm thick CZT) is provided for the cathodes and an optional capacitive decoupling circuit allows reading the induced cathode signal as well as the anode signals. The overall dimension of the D-Matrix*^ aggregator module (AM) 20 with 4 GMs 21 (CZT detectors, 0.5 cm thick) and readout electronics is about 4.4 cm×4.4 cm×5 cm thick. This AM 20 can be tiled to comprise various sized arrays to constitute flat panels, curved panels, rings, ellipses, or other structures as will be disclosed in this specification. Some of the features of the AM 20 are listed in Table 1.

One of the advantages of CZT gamma detectors is that they occupy a smaller volume than scintillators and PMTs, so that CZT gamma cameras can be shielded by far less volume and weight of heavy metal, such as lead (Pb) or tungsten (W). Thus a SPECT system gantry designed specifically for a CZT gamma camera can be smaller and lighter than a conventional SPECT gantry. It may have a smaller footprint and fit into a smaller examination room.

Furthermore, the energy resolution of a CZT gamma camera, as tabulated in Table 2, is much better (about 4% vs about 9.6% for NaI). Practically, this means that a narrower energy window can be used to for the photopeak planar projection images that are reconstructed into 3D SPECT images. This narrower energy window will discriminate against scattered gamma photons which blur the SPECT image. Thus, the final image contrast should significantly improve in a CZT camera compared to a scintillation gamma camera.

FIG. 2 depicts one such array 22 of AMs 20 (only two of 108 are labelled) in a size typical of flat panel gamma cameras used in general purpose medical SPECT. The illustrative array 22 comprises nine rows and 12 columns of AMs 20 forming a flat panel gamma camera 22 with dimensions of about 39.6 cm×52.8 cm. This illustrative arrangement comprises nine×12 108 AMs and (nine×22)× (12×22)=198×264=52,272 pixels, as tabulated in Table 2.

The original gamma camera built by Hal Anger in 1957 was a flat panel detector with a circular field of view. All commercial clinical gamma cameras have been derivatives of the original flat panel, although the field of view became rectangular in the 1980s when 3D tomographic image reconstruction from SPECT became practical. There have been several attempts to use curved scintillation cameras for brain or heart imaging applications, but none have been commercially successful. Several small-animal preclinical SPECT sJ stems were built using CZT modules in a ring, but these have not been sold in any successful quantities. Nevertheless, modular detector assemblies, such as the Aggregator Module, AJ'vI 20, of FIGS. 1 and 2 are amenable to forming a curved arcuate surface, or ring, or ellipse of detectors.

Figure 3:
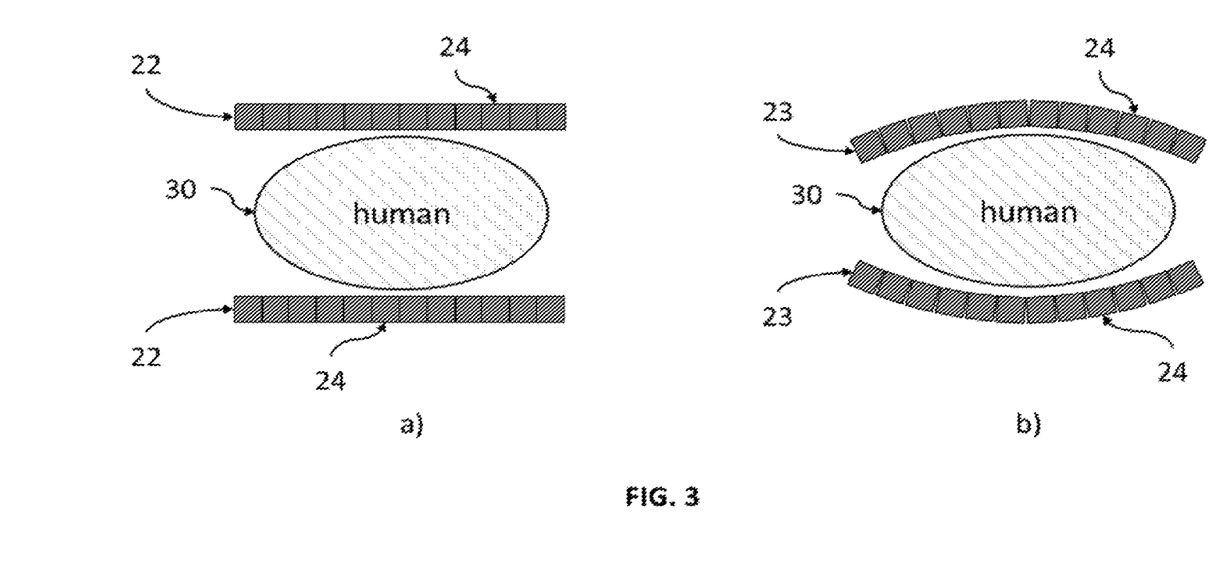
FIG. 3 illustrates a transaxial view of a human body surrounded by two opposed SPECT scanning CZT gamma cameras in either a flat panel or concave curved panel configuration.

FIGS. 3(a) and 3(b) illustrate this design option for a curved detector surface. FIG. 3(a) illustrates a transaxial cross-section (view from the patient's feet) of a dual-detector SPECT system with a human body 30 as the example object being imaged by gamma emission. Both detector arrays 22 in FIG. 3a, as in FIG. 2, are shown in cross-section with 12 columns 24 illustrated by gray boxes. By reference to FIG. 2, it is apparent that each column 24 comprises nine AMs 20 with length about 39.6 cm. Not shown explicitly are collimators, radiation shielding, and readout electronics, but these elements are well known by those of skill in the art. FIG. 3(b) illustrates curved arcuate surface detectors 23 that could be formed by placing the columns 24 of AMs 20 along a curved surface that roughly follows the contour of a typical human body.

A gamma camera could be designed to mechanically transform between the flat panel configuration of FIG. 3(a) and the curved panel configuration of FIG. 3(b). It is anticipated that the curvature could be fixed or variable. The reconstruction would be easier for a fixed curvature, but if the position of each detector is tracked mechanically or by other means, then the iterative reconstruction software could accommodate "body contouring" with variable curve panels. As will be apparent to those skilled in the art, the hinge points for such a transformation would depend upon the collimation scheme employed. For example, if parallel hole collimators were attached to each CZT detector column 24, then the hinge points would be at the front face of the collimator columns. However, if multiple-pinhole collimation were employed, the hinge points would be at the front face of the CZT detectors 21 of FIG. 1.

Figure 5:
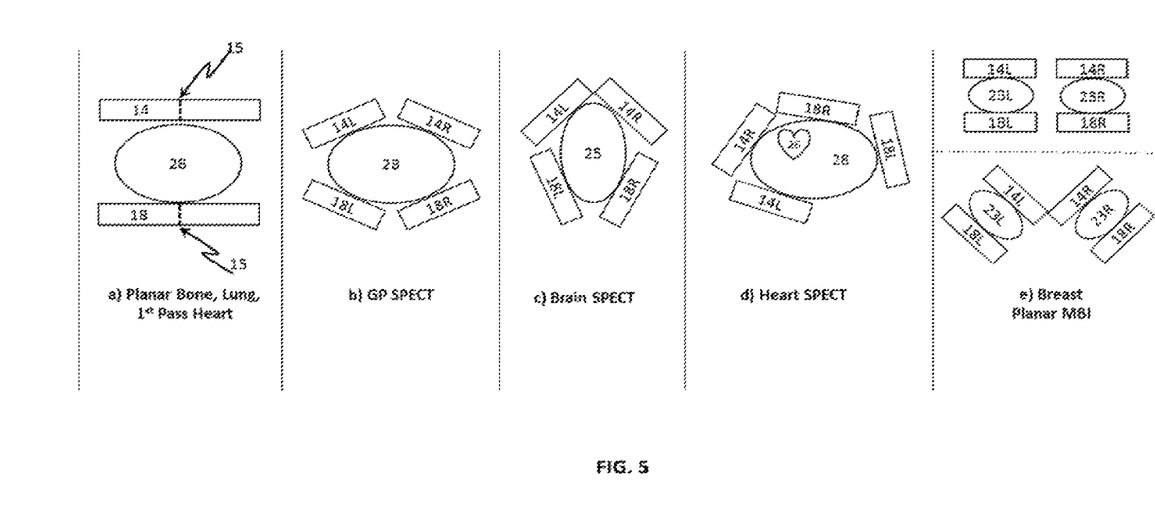
FIG. 5 illustrates an embodiment of the present invention as a cross-sectional view of gamma cameras and a body for various clinical SPECT imaging applications.
Figure 6:
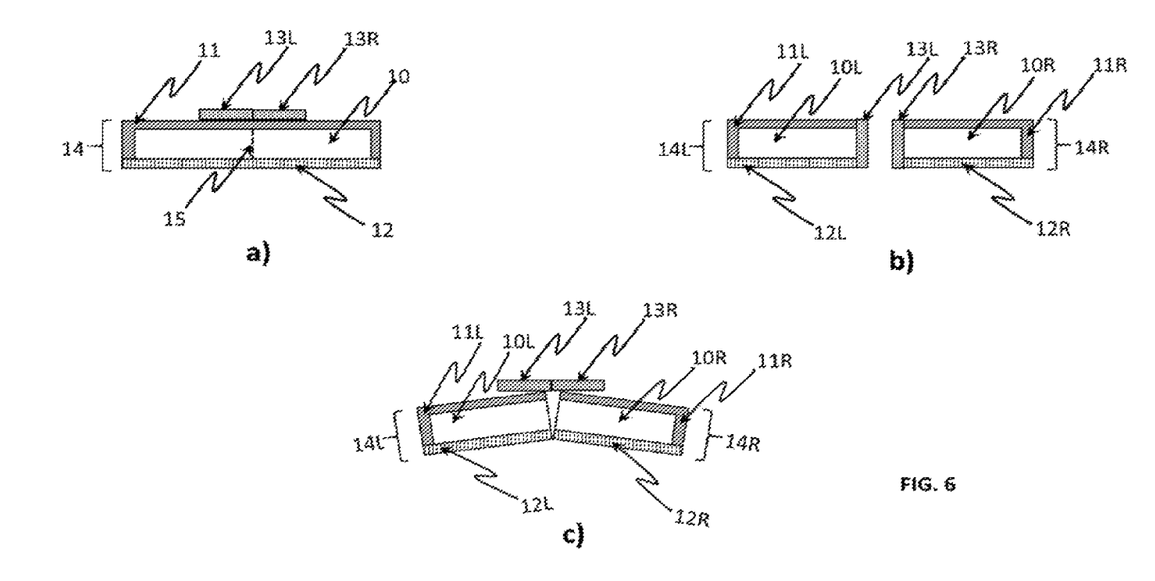
FIG. 6 illustrates an embodiment of the present invention as a cross-sectional view of a pixelated gamma camera that is configured to subdivide into two smaller gamma cameras.
Figure 7:
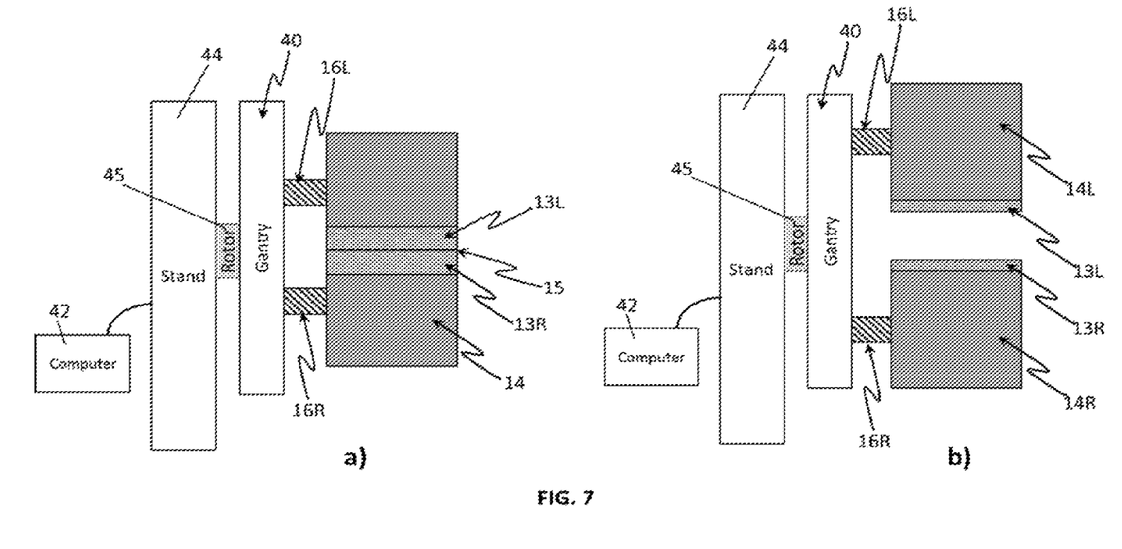
FIG. 7 illustrates an embodiment of the present invention as a side view of a pixelated gamma camera that is configured to subdivide into two smaller gamma cameras.

It is intended that the concept of arcuate detector panels should be applied to other possible embodiments, such as those in FIGS. 5, 6, and 7. Wherever a flat panel gamma camera is illustrated, an arcuate panel gamma camera can be substituted within the spirit and scope of this invention.

The smaller square pixels of a CZT gamma camera can also be used to advantage compared to the overlapping Gaussian pixels of a scintillation gamma camera. Collimators can be designed (not the subject of the present invention) to optimize the spatial resolution and efficiency of the detector-collimator system, again improving the image contrast. By way of illustration, Table 3 shows a comparison of typical hexagonal parallel-hole collimators, as used in typical SPECT systems, and some possible pixel-registered square-hole collimators. These design concepts have not been optimized, but are illustrative of the performance achievable with such pixelated CZT specific collimators.

TABLE 3

Comparison of typical SPECT collimators and potential CZT-specfic collimators.

| Type | Hole Shape | Size (mm) | Septa (mm) | Length (mm) | Penetration @ 140 keV | Efficiency' (cpm/mCi) | Resolution (mm) @ 0 cm | Resolution (mm) @ 10 cm | Resolution (mm) @ 20 cm |
|---|---|---|---|---|---|---|---|---|---|
| typical LEGP | Hexa-gOnal | 1.40 | 0.18 | 24.1 | 2.1% | 277 | 3.9 | 8.9 | 14.7 |
| Typic al-LEHR | Hexa- | 1.22 | 0.15 | 27.0 | 1.7% | 168 | 3.7 | 7.4 | 11.9 |
| LEG P-CZT | Squnre | 1.80 | 0.20 | 31.0 | 1.6% | 356 (+29%) | 2.2 | 8.9 | 15.6 |
| LEH R-CZT | Square | 1.85 | 0.1.5 | 40.9 | 1.8% | 226 (+35%) | 2.2 | 7.4 | 12.6 |

Figure 4:
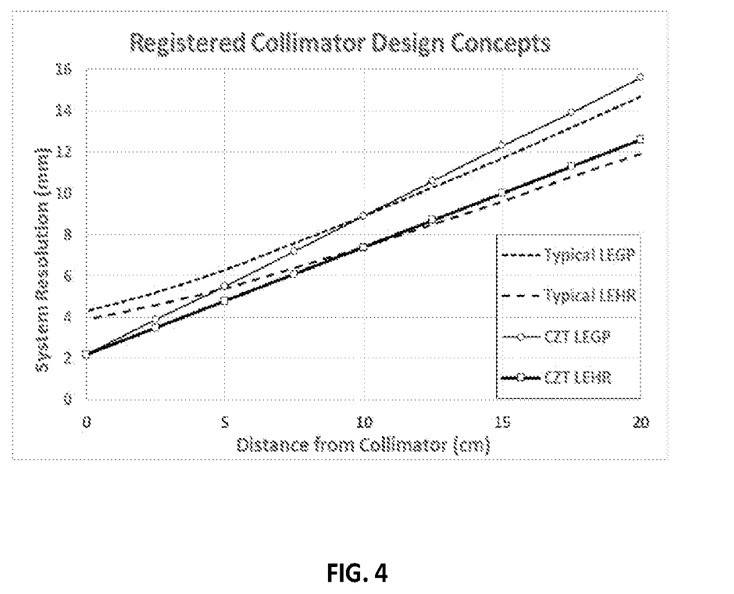
FIG. 4 is a graph comparing the planar system resolution for scintillator and CZT gamma cameras using registered square-hole collimator concepts.

FIG. 4 shows graphically the comparison of the four collimators shown in Table 3. The dashed curves represent the system resolution for typical LEGP (Low Energy General Purpose, short dash) and LEHR (Low Energy High Resolution, longer dash) hexagonal parallel-hole lead (Pb) collimators. By way of illustration, the solid lines represent the system resolution for two potential designs for pixel-registered square-parallel-hole lead (Pb) collimators. The thinner solid line with open circle markers represents the LEGP-CZT collimator response; the thicker solid line with open square markers represents the LEHR-CZT collimator response. The system resolution at 10 cm distance from the face of the collimator was matched for the two LEGP and two LEHR collimators, as an example of a possible design. Of course the resolution as a function of distance from the collimator can be traded off for system efficiency (sensitivity). For the particular choice illustrated in FIG. 4 and TAB. 3, the registered LEGP-CZT is 29% more efficient than the typical clinical hexagonal hole LEGP collimator. Likewise, the LEHR-CZT is 35% more efficient than the typical clinical hexagonal hole LEHR collimator. The optimization of the design depends on the application task and could be accomplished by Monte Carlo modeling simulation of the system response coupled with iterative reconstruction employing a full physics description of the detector-collimator response.

As will be apparent to one skilled in the art, a pixel-registered collimator response has no significant dependence on the detector spatial resolution, hence the system resolution response function is approximately a straight line. In contrast, for a scintillator with Gaussian pixels, the system resolution is a quadrature summation of the detector and collimator resolutions, hence the resolution response function is approximately parabolic. The advantage for closer distances belongs to the CZT gamma camera with pixel-registered collimator. It will be apparent to one skilled in the art that the spatial resolution for a square-hole collimator is not isotropic in the plane. In our experience with such collimators as used in Molecular Breast Imaging (MBI), this off-axis resolution is not a significant issue.

As will be apparent to one skilled in the art, pixelated CZT detectors are a preferred embodiment of the present invention, but some of the advantages can be obtained with pixelated scintillator gamma cameras. The pixels may be made of NaI, CsI, or LaBr, for example, and the scintillation light readout may be achieved by optically-coupled photo-detectors, such as vacuum PMTs, avalanche photodiodes, position-sensitive photomultiplier tubes, or Silicon photomultipliers, for example. None of these alternative pixelated cameras can match CZT in energy resolution, spatial resolution, and compactness of form. Nevertheless, it is possible to beneficially apply the principles disclosed in the present specification to such alternative pixelated gamma cameras.

FIG. 5 illustrates an embodiment of the present invention as a cross-sectional view of gamma cameras and a body for various clinical SPECT imaging applications. In FIGS. 5a), 5b), and 5d) the approximately ellipsoidal cross-section of the torso of a body 28 is being imaged by multiple gamma cameras 14 and 18. In FIG. 5c) the head and brain 25 is being imaged, while in 5d) the heart 26 and in 4e) the breasts 23 are being imaged. The gamma cameras 14 and 18 (and 14L, 14R, 18L, 18R) comprise pixelated gamma sensors, readout electronics, radiation shielding, and collimation, as will be discussed in FIGS. 6 and 7 below.

In FIG. 5a) the dashed lines 15 represents a plane bisecting the transaxial width of the full-FOV gamma cameras 14 and 18. It is at this plane that each of the two pixelated gamma cameras 14 and 18 have been configured to separate into two smaller FOV cameras (14L and 14R, 18L and 18R). In a special case, both smaller FOV cameras are equal in width. One with skill in the art will recognize that such subdivisions can occur in multiple locations and that the resulting smaller FOV cameras need not all be the same size. In FIGS. 5b) through 5e), the smaller FOV cameras are shown, by way of illustration, as four half-FOV cameras 14L, 14R, 18L, 18R with left and right halves.

The drawings in FIG. 5 show a snapshot in time of a SPECT data acquisition. Multiple projection views must be acquired to reconstruct a 3D SPECT image and the required orbital motion of the gamma cameras 14 and 18 (or 14L, 14R, 18L, and 18R) is not illustrated here, because it is well-known to those of skill in the art. Further, the drawings show the front surface of the gamma cameras 14 and 18 in contact with the body 28, head 25, or breasts 23. This is a preferred geometry in which the gamma camera is positioned as close as possible to the volume of interest. However, when the gamma cameras 14 and 18 are moved to the next imaging view, they must first back away from the body 28, head 25, or breasts 23, then move to the new viewing position, and then move to close proximity to the body 20, head 25, or breasts 23. This procedure is known by those skilled in the art as "body contouring" and for safety reasons with large gamma cameras 14 and 18, the closest approach to the body 20, head 25, or breasts 23 (as detected by infrared beams, for example) may be limited to several cm. With smaller FOV gamma cameras 14L, 14 R, 18L, and 18R it will be safer to approach the body 20, head 25, or breasts 23 more closely, thus improving the reconstructed spatial image resolution.

FIG. 6a) illustrates an embodiment of the present invention as a cross-sectional view of a pixelated gamma camera 14 that is configured to subdivide at the plane 15 into two smaller gamma cameras 14L and 14R as illustrated in FIGS. 6b) and 6c). The gamma camera 14 comprises a pixelated detector with readout electronics 10, radiation shielding 11, and collimation 12, shown by way of example as a parallel hole collimator. In a preferred embodiment, the detector 10 comprises pixelated CZT direct conversion semiconductor modules, such as the D-Matrix 20 shown in FIG. 1. The readout electronics associated with the pixelated detector 10 comprises ASICs, ADCs, and digital communications that transmit to a data acquisition computer (42, FIG. 7) a list of gamma photon detection event packets containing at least 2D position and energy. As in FIG. 5, the dashed line 15 marks a plane of potential separation where the detector 10, shielding 11, and collimator 12 can subdivide to form two smaller FOV gamma cameras 14L and 14R.

As will be apparent to those skilled in the art, a subdivided detector requires additional radiation shielding 13L and 13R to cover the edge of the exposed detector 10L and 10R. This additional shielding 13L and 13R can be emplaced robotically or manually. Of course, this additional shielding 13L and 13R must be removed before the subdivided gamma cameras 14L and 14R can be rejoined into a full-FOV gamma camera 14. FIG. 6a) shows this additional edge shielding attached to the large-FOV general-purpose gamma camera 14 in a position where it can be deployed when the transformable camera 14 is subdivided. FIG. 6b) illustrates the case in which the two small-FOV cameras 14L and 14R formed by subdividing the full-FOV camera 14 are separated completely and form independent gamma cameras. The additional radiation shielding 13L and UR has been moved (preferentially automated) to cover the exposed ends of the subdivided gamma cameras. A different case is illustrated in FIG. 6c) in which the two small-FOV cameras 14L and 14R are not completely separated, but are held together at a hinge line to keep some dependence on location and orientation between the two small-FOV cameras. In this case, the additional shielding UL and UR would cover the wedge-shaped space between the two small-FOV cameras FIG. 7a) illustrates an embodiment of the present invention as a plan view of a pixelated gamma camera 14 that is configured to subdivide at the plane 15 into two smaller gamma cameras 14L and 14R as in FIG. 7b). The additional radiation shielding UL and 13R covers the exposed edges of the detectors 10L and 10R. One further essential mechanical feature is illustrated in FIG. 7, namely the mechanical supports 16L and 16R. These mechanical supports can take various forms in the contemplated embodiments of this present invention. In one embodiment, the mechanical supports 16L and 16R would connect to a standard SPECT system gantry ring 40 and would be capable of radial and azimuthal (rotating) motions in addition to providing pivoting motion along the mechanical support axis 16L or 16R to aim the camera away from the system gantry axis of rotation. In another embodiment, the mechanical supports 16L and 16R would comprise articulated arms to enable manual or robotic positioning of the gamma cameras (14 or 14L and 14R) in many positions surrounding the body, as illustrated in FIG. 5 for a sampling of potential clinical applications.

As one skilled in the art will understand, a standard SPECT system is required to support the transformable gamma cameras and there are multiple geometric forms for such systems. In essence, such systems contain a stand 44 that supports a rotor 45 and gantry 40. The transformable gamma cameras 14 or 14L and 14R are supported by mechanical supports 16L and 16R. All motions of the system (rotations, translations, robotic positioning) including a patient bed (not shown) are controlled by a computer 42, which also acquires digital data from the gamma cameras 14 or 14L and 14R, reconstructs 2D planar and 3D SPECT images, and display s the resulting images for medical interpretation.

In summary, this invention provides in one embodiment an innovative design for a SPECT system that robotically transforms into an adaptable geometry that is more optimized for various clinical applications than the state-of-the-art SPECT systems with two large-FOV flat panel scintillator gamma cameras. This embodiment provides means to subdivide the large full-FOV gamma cameras 14 and 18 into at least four smaller FOV gamma cameras 14L, 14a 18L, and 18R, and to position these around the body in more efficient geometries for SPECT imaging. The most apparent advantage is that the efficiency of acquisition can be approximately doubled. Also, the spatial resolution of reconstructed images can be improved by placing more of the detector volume closer to the imaged volume of interest.

Figure 8:
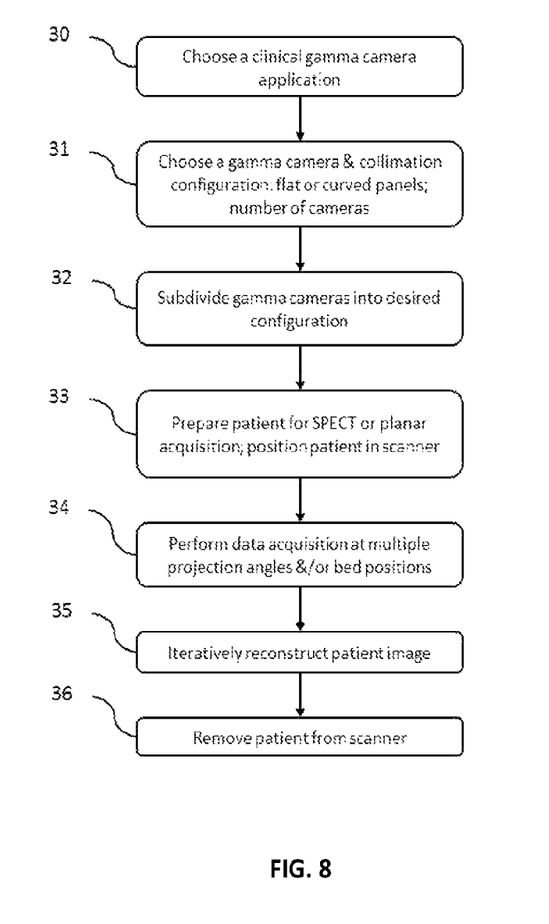
FIG. 8 is a process flow diagram depicting an illustrative method for applying any of the embodiments of the present invention in a clinical setting.

FIG. 8 is a process flow diagram depicting an illustrative method for applying any of the embodiments of the present invention in a clinical setting. Assuming that a SPECT system with one or more transformable gamma cameras has been designed, built, and installed in a nuclear medicine ("molecular imaging") clinic, then the steps illustrated in FIG. 8 would be followed to utilize such an innovative system. The first step 30 for each patient examination is to choose a clinical application. Typically, one application is employed for each patient, but it is possible to conduct two or more sequential studies in the same patient during a single examination. If that is the case, this process flow is repeated for each clinical application, such as brain blood flow, lung perfusion/ventilation, myocardial perfusion, or whole-body bone (planar or SPECT).

The next step 31 is to match the clinical application with an optimal configuration for the gamma cameras and collimators. Choices must be made such as flat or curved panels, number of gamma cameras, and type of collimation. Typically, such choices will be entered into a graphical user interface which will associate preferred configurations provided by the manufacturer for each clinical application. After selection of a desired configuration, the scanner will transform automatically into the desired configuration, subdividing the large general-purpose gamma camera into smaller subsets of the large tiled array, as shown in step 32. This transformation process may be entirely robotic or it may be manually assisted. For example, collimators may need to be exchanged and additional radiation shielding may need to be attached or removed.

The next step 33 is patient preparation. This step may, of course, be performed before or in parallel with the previous steps. After the scanner is properly configured (step 32) and the patient has been prepared with an injection of a radiotracer, then the patient will be positioned on the scanner bed and moved into position for the first of multiple projection images.

Step 34 is data acquisition. The multiple transformed gamma cameras are positioned around the patient's body 28, head 25, or breasts 23 and a single planar projection is acquired (potentially a different plane for each of the multiple cameras). Then this step is repeated multiple times by moving the cameras robotically to different angles around the patient and different camera orientations (such as all focused on the heart 26). After all data has been acquired, then step 35 is performed in which the computer reconstructs and then displays and stores the patient SPECT image. Also after data acquisition, step 36 can be performed to remove the patient from the SPECT scanner. Obviously, steps 35 and 36 can be performed in either order or simultaneously.

While preferred embodiments of the present invention are shown and described, it is envisioned that those skilled in the art may devise various modifications of the present invention without departing from the spirit and scope of the appended claims.

What is claimed is:

1. A gamma camera system comprising:
a stand, a rotatable gantry supported by the stand,
a transformable gamma camera connected by mechanical supports to the rotatable gantry and comprising groups of tiled arrays of gamma detectors, and a collimator for each group of tiled arrays of gamma detectors, and radiation shielding;
the transformable gamma camera being configured to subdivide at a point which bisects a transaxial width of the transformable gamma camera into a plurality of subdivided gamma cameras, each of the subdivided gamma cameras having at least one of the groups of tiled arrays of gamma detectors, the radiation shielding, configured to cover an exposed edge of the subdivided gamma cameras, and corresponding collimator, wherein the subdivision into a plurality of subdivided gamma cameras facilitates contouring with a region of interest for a spatial resolution, wherein the subdivision defines an independently positioned field of view of the region of interest for each of the plurality of subdivided cameras.

2. The transformable gamma camera of claim 1, wherein the tiled array of gamma detectors comprises at least one of: a flat panel and a curved panel.

3. The transformable gamma camera of claim 1, wherein the tiled array of gamma detectors comprises at least one of: a scintillator with an optically-coupled photodetector, and a semiconductor direct conversion detector.

4. The transformable gamma camera of claim 1, wherein the tiled array of gamma detectors comprises a sparsely populated tiled array of gamma detectors.

5. The transformable gamma camera of claim 1, wherein the mechanical supports are configured to position the transformable gamma camera or the plurality of subdivided gamma cameras.

6. The transformable gamma camera of claim 1, wherein the plurality of subdivided gamma cameras that can be independently positioned for breast imaging are configured for compression of the breasts between the plurality of subdivided gamma cameras.

7. The transformable gamma camera of claim 1, wherein at least one of the mechanical supports is configured for rotation about a mechanical support axis of at least one of the subdivided gamma cameras.

8. A transformable gamma camera comprising:
a plurality of groups of tiled arrays of gamma detectors and, a collimator for each group of tiled arrays of gamma detectors, and radiation shielding;
the transformable gamma camera being configured to subdivide at a point which bisects a transaxial width of the transformable gamma camera into a plurality of subdivided gamma cameras, each of the subdivided gamma cameras having at least one of the groups of tiled arrays of gamma detectors, the radiation shielding, configured to cover an exposed edge of the subdivided gamma cameras, and corresponding collimator, wherein the subdivision into a plurality of subdivided gamma cameras facilitates contouring with a region of interest for a spatial resolution, wherein the subdivision defines an independently positioned field of view of the region of interest for each of the plurality of subdivided cameras.

9. The transformable gamma camera of claim 8, wherein the tiled array of gamma detectors comprises at least one of: a flat panel and a curved panel.

10. The transformable gamma camera of claim 8 wherein the tiled array of gamma detectors comprises at least one of:
a scintillator with an optically-coupled photodetector, and
a semiconductor direct conversion detector.

11. The transformable gamma camera of claim 8, wherein the tiled array of gamma detectors comprises a sparsely populated tiled array of gamma detectors.

12. The gamma camera of claim 8, wherein the collimator comprises a parallel square-hole collimator.

13. An imaging method, comprising:
a step of contouring a transformable gamma camera with a region of interest for a spatial resolution by subdividing the transformable gamma camera at a point which bisects a transaxial width of the transformable gamma camera into a plurality of subdivided gamma cameras, the step further comprising covering with radiation shielding, an exposed edge of the subdivided gamma cameras;
the transformable gamma camera comprising:
groups of tiled arrays of gamma detectors, and a collimator for each group of tiled arrays of gamma detectors, and the radiation shielding;
each of the subdivided gamma cameras comprising:
at least one of the groups of tiled arrays of gamma detectors, the radiation shielding covering the exposed edge, and corresponding collimator; and
wherein the subdivision defines an independently positioned field of view of the region of interest for each of the plurality of subdivided cameras.

14. The imaging method of claim 13 further comprising at least one of the steps of:
choosing a clinical application and an optimal configuration of a plurality of gamma cameras and collimators,
preparing a patient for gamma photon imaging data acquisition,
positioning the patient in a scanner,
acquiring one or more gamma photon image projections,
reconstructing the gamma photon images, and
removing the patient from the scanner.

15. The imaging method of claim 13, wherein the tiled array of gamma detectors comprises at least one of: a flat panel and a curved panel.

16. The imaging method of claim 13, wherein the tiled array of gamma detectors comprises at least one of:
a scintillator with an optically-coupled photodetector, and
a semiconductor direct conversion detector.

17. The transformable gamma camera of claim 13, wherein the tiled array of gamma detectors comprises a sparsely populated tiled array of gamma detectors.

18. The imaging method of claim 13, wherein the plurality of subdivided gamma cameras that can be independently positioned for breast imaging are configured for compression of the breasts between the plurality of subdivided gamma cameras.

19. The imaging method of claim 13, wherein the collimator comprises a parallel square-hole collimator.

* * * * *